(12) United States Patent
Klimowicz et al.

(10) Patent No.: US 6,554,201 B2
(45) Date of Patent: Apr. 29, 2003

(54) INSERT MOLDED AEROSOL GENERATOR AND METHODS

(75) Inventors: Michael A. Klimowicz, Los Altos, CA (US); Brian S. Thornton, Santa Clara, CA (US)

(73) Assignee: Aerogen, Inc., Sunnyvale, CA (US)

( * ) Notice: Subject to any disclaimer, the term of this patent is extended or adjusted under 35 U.S.C. 154(b) by 0 days.

(21) Appl. No.: 09/848,111

(22) Filed: May 2, 2001

(65) Prior Publication Data

US 2002/0162898 A1 Nov. 7, 2002

(51) Int. Cl.[7] .............................................. B05B 17/04
(52) U.S. Cl. ....................................... 239/4; 239/102.1
(58) Field of Search ......................... 239/3, 4, 10, 102.1, 239/102.2; 128/200.23

(56) References Cited

U.S. PATENT DOCUMENTS

| | | | |
|---|---|---|---|
| 3,558,052 A | 1/1971 | Dunn | 293/3 |
| 3,738,574 A | 6/1973 | Guntersdorfer et al. | 239/102 |
| 3,790,079 A | 2/1974 | Berglund et al. | 239/3 |
| 3,804,329 A | 4/1974 | Martner | 239/4 |
| 3,812,854 A | 5/1974 | Michaels et al. | 128/194 |
| 3,950,760 A | 4/1976 | Stromberger et al. | 346/140 |
| 3,958,249 A | 5/1976 | DeMaine et al. | 346/1 |
| 3,983,740 A | 10/1976 | Danel | 73/12 |
| 4,005,435 A | 1/1977 | Lundquist et al. | 346/1 |
| 4,059,384 A * | 11/1977 | Holland et al. | 425/414 |
| 4,119,096 A | 10/1978 | Drews | 128/194 |
| 4,159,803 A | 7/1979 | Cameto et al. | 239/102 |
| 4,226,236 A | 10/1980 | Genese | |
| 4,240,081 A | 12/1980 | Devitt | 346/75 |
| 4,261,512 A | 4/1981 | Zierenberg | 239/102 |
| 4,268,460 A | 5/1981 | Boiarski | 261/1 |
| 4,294,407 A | 10/1981 | Reichl et al. | 239/102 |
| 4,300,546 A | 11/1981 | Kruber | 128/200 |
| 4,301,093 A | 11/1981 | Eck | 261/1 |
| 4,334,531 A | 6/1982 | Reichl et al. | 128/200.14 |
| 4,336,544 A | 6/1982 | Donald et al. | 346/1.1 |
| 4,338,576 A | 7/1982 | Takahashi et al. | 331/67 |
| 4,368,476 A | 1/1983 | Uehara et al. | 346/104 R |
| 4,389,071 A | 6/1983 | Johnson, Jr. et al. | 299/14 |
| 4,408,719 A | 10/1983 | Last | 239/102 |
| 4,431,136 A | 2/1984 | Janner et al. | 239/102 |
| 4,454,877 A | 6/1984 | Miller et al. | 128/200.21 |
| 4,465,234 A | 8/1984 | Maehara et al. | 239/102 |
| 4,474,251 A | 10/1984 | Johnson, Jr. | 175/67 |

(List continued on next page.)

FOREIGN PATENT DOCUMENTS

| | | | |
|---|---|---|---|
| CH | 477 885 | * | 10/1969 |
| CH | 555 681 | * | 9/1974 |
| EP | 0 049 636 A1 | | 4/1982 |
| EP | 0 103 161 A2 | | 3/1984 |

(List continued on next page.)

OTHER PUBLICATIONS

Berglund, R.N., et al. Generation of Monodisperse Aerosol Standards. Environ. Sci. Technology 7:2:147 (1973).*
Allen, T. Particle Size Measurement. Chapman and Hall pp. 167–169 (1981).*
Ueha, S., et al. Mechanism of Ultrasonic Atomization Using a Multi–Pinhole Plate. J. Acoust. Soc. Jpn. (E) 6,1:21 (1985).*

(List continued on next page.)

Primary Examiner—Lisa A. Douglas
(74) Attorney, Agent, or Firm—Townsend and Townsend and Crew LLP

(57) ABSTRACT

A method for producing an aerosol generator utilizes a vibratable member having a plurality of apertures for producing liquid droplets upon vibration of the vibratable member. A support member is injection molded about the vibratable member, and a vibratable element is placed in vibrational communication with the vibratable member.

17 Claims, 6 Drawing Sheets

U.S. PATENT DOCUMENTS

| | | | |
|---|---|---|---|
| 4,474,326 A | 10/1984 | Takahashi | 239/102 |
| 4,475,113 A | 10/1984 | Lee et al. | 346/1.1 |
| 4,479,609 A | 10/1984 | Maeda et al. | 239/102 |
| 4,530,464 A | 7/1985 | Yamamoto et al. | 239/102 |
| 4,533,082 A | 8/1985 | Maehara et al. | 239/102 |
| 4,539,575 A | 9/1985 | Nilsson | 346/140 R |
| 4,544,933 A | 10/1985 | Heinzl | 346/140 R |
| 4,546,361 A | 10/1985 | Brescia et al. | 346/140 R |
| 4,550,325 A | 10/1985 | Viola | 346/140 R |
| 4,591,883 A | 5/1986 | Isayama | 346/140 R |
| 4,593,291 A | 6/1986 | Howkins | 346/1.1 |
| 4,605,167 A | 8/1986 | Maehara | 239/102 |
| 4,620,201 A | 10/1986 | Heinzl et al. | 346/140 R |
| 4,628,890 A | 12/1986 | Freeman | 123/593 |
| 4,632,311 A | 12/1986 | Nakane et al. | 239/101 |
| 4,659,014 A | 4/1987 | Soth et al. | 239/102.2 |
| 4,681,264 A | 7/1987 | Johnson, Jr. | 239/589.1 |
| 4,702,418 A | 10/1987 | Carter et al. | 239/101 |
| 4,722,906 A | 2/1988 | Guire | |
| 4,753,579 A | 6/1988 | Murphy | 417/322 |
| 4,790,479 A | 12/1988 | Matsumoto et al. | 239/102.2 |
| 4,793,339 A | 12/1988 | Matsumoto et al. | 128/200.16 |
| 4,796,807 A | 1/1989 | Bendig et al. | 239/102.2 |
| 4,799,622 A | 1/1989 | Ishikawa et al. | 239/102.2 |
| 4,826,759 A | 5/1989 | Guire | |
| 4,828,886 A | 5/1989 | Hieber | 427/422 |
| 4,850,534 A | 7/1989 | Takahashi et al. | 239/102.2 |
| 4,865,006 A | 9/1989 | Nogi et al. | 123/590 |
| 4,877,989 A | 10/1989 | Drews et al. | 310/323 |
| 4,888,516 A | 12/1989 | Daeges et al. | 310/323 |
| 4,968,299 A | 11/1990 | Ahlstrand et al. | |
| 4,973,493 A | 11/1990 | Guire | |
| 4,976,259 A | 12/1990 | Higson et al. | |
| 4,979,959 A | 12/1990 | Guire | |
| 4,994,043 A | 2/1991 | Ysebaert | |
| 5,002,582 A | 3/1991 | Guire et al. | |
| 5,021,701 A | 6/1991 | Takahashi et al. | 310/345 |
| 5,063,396 A | 11/1991 | Shiokawa et al. | 346/140 R |
| 5,063,922 A | 11/1991 | Hakkinen | 128/200.16 |
| 5,073,484 A | 12/1991 | Swanson et al. | |
| 5,076,266 A | 12/1991 | Babaev | 128/200.36 |
| 5,080,649 A | 1/1992 | Vetter | |
| 5,086,785 A | 2/1992 | Gentile et al. | |
| 5,115,803 A | 5/1992 | Sioutas | 128/200.23 |
| 5,139,016 A | 8/1992 | Waser | 128/200.16 |
| 5,140,740 A | 8/1992 | Weigelt | |
| 5,152,456 A | 10/1992 | Ross et al. | 239/102.2 |
| 5,157,372 A | 10/1992 | Langford | |
| 5,164,740 A | 11/1992 | Ivri | 346/1.1 |
| 5,170,782 A | 12/1992 | Kocinski | 128/200.16 |
| 5,186,164 A | 2/1993 | Raghuprasad | |
| 5,186,166 A | 2/1993 | Riggs et al. | |
| 5,198,157 A | 3/1993 | Bechet | 264/9 |
| 5,217,492 A | 6/1993 | Guire et al. | |
| 5,258,041 A | 11/1993 | Guire et al. | |
| 5,261,601 A | 11/1993 | Ross et al. | 239/102.2 |
| 5,263,992 A | 11/1993 | Guire | |
| 5,297,734 A | 3/1994 | Toda | 239/102.2 |
| 5,299,739 A | 4/1994 | Takahashi et al. | 239/102.2 |
| 5,309,135 A | 5/1994 | Langford | |
| 5,312,281 A | 5/1994 | Takashashi et al. | 446/25 |
| 5,320,603 A | 6/1994 | Vetter et al. | |
| 5,347,998 A | 9/1994 | Hodson et al. | 128/200.23 |
| 5,414,075 A | 5/1995 | Swan et al. | |
| 5,415,161 A | 5/1995 | Ryder | 128/200.23 |
| 5,452,711 A | 9/1995 | Gault | |
| 5,477,992 A | 12/1995 | Jinks et al. | 222/402.16 |
| 5,487,378 A | 1/1996 | Robertson et al. | 128/200.16 |
| 5,512,329 A | 4/1996 | Guire | |
| 5,512,474 A | 4/1996 | Clapper et al. | |
| 5,515,841 A | 5/1996 | Robertson et al. | 128/200.16 |
| 5,515,842 A | 5/1996 | Ramseyer et al. | |
| 5,518,179 A | 5/1996 | Humberstone et al. | 239/102.2 |
| 5,533,497 A | 7/1996 | Ryder | 128/200.21 |
| 5,563,056 A | 10/1996 | Swan et al. | |
| 5,579,757 A | 12/1996 | McMahon et al. | 128/200.21 |
| 5,586,550 A | 12/1996 | Ivri et al. | 128/200.16 |
| 5,637,460 A | 6/1997 | Swan et al. | |
| 5,654,162 A | 8/1997 | Guire et al. | |
| 5,654,460 A | 8/1997 | Rong | |
| 5,665,068 A | 9/1997 | Takamura | |
| 5,692,644 A | 12/1997 | Gueret | |
| 5,707,818 A | 1/1998 | Chudzik et al. | |
| 5,714,360 A | 2/1998 | Swan et al. | |
| 5,714,551 A | 2/1998 | Bezwada et al. | |
| 5,718,222 A | 2/1998 | Lloyd et al. | |
| 5,744,515 A | 4/1998 | Clapper | |
| 5,758,637 A | 6/1998 | Ivri et al. | 128/200.16 |
| 5,893,515 A | 4/1999 | Hahn et al. | |
| 5,938,117 A | 8/1999 | Ivri | 239/4 |
| 6,012,450 A | 1/2000 | Rabsamen | |
| 6,014,970 A | 1/2000 | Ivri et al. | |
| 6,085,740 A | 7/2000 | Ivri et al. | |

FOREIGN PATENT DOCUMENTS

| | | | |
|---|---|---|---|
| EP | 0 134 847 A1 | | 3/1985 |
| EP | 0 178 925 | * | 4/1986 |
| EP | 0 542 723 A2 | | 5/1993 |
| EP | 0 476 991 B1 | * | 3/1995 |
| FR | 2 692 569 A1 | * | 6/1992 |
| GB | 973458 | | 10/1964 |
| GB | 1454597 | | 11/1976 |
| GB | 2 073 616 A | * | 10/1981 |
| GB | 2 101 500 | * | 1/1983 |
| GB | 2 177 623 A | * | 1/1987 |
| GB | 2 240 494 A | * | 8/1991 |
| GB | 2 272 389 A | * | 5/1994 |
| GB | 2 279 571 A | * | 1/1995 |
| JP | 57-23852 | | 2/1982 |
| JP | 57-105608 | | 7/1982 |
| JP | 58-61857 | | 4/1983 |
| JP | 58-139757 | | 8/1983 |
| JP | 60-4714 A | | 1/1985 |
| JP | 61-8357 A | | 1/1986 |
| JP | 61-215059 A | | 9/1986 |
| JP | 2-135169 | | 5/1990 |
| JP | 2-189161 | | 7/1990 |
| WO | WO 92/07600 | * | 5/1992 |
| WO | WO 92/11050 | * | 7/1992 |
| WO | WO 93/01404 | * | 1/1993 |
| WO | WO 96/09229 | * | 3/1996 |
| WO | WO 96/31289 | * | 10/1996 |
| WO | WO 97/07896 | * | 3/1997 |
| WO | WO 99/63946 | * | 12/1999 |

OTHER PUBLICATIONS

Maehara, N., et al. Influence of the Vibrating System of a Multipinhole–plate Ultrasoic Nebulizer on Its Performance. Review of Scientific Instruments, 57 (11), Nov. 1986, pp. 2870–2876.*

Maehara, N., et al. Optimum Design Procedure for Multi–Pinhole–plate Ultrasonic Atomizer. Japanese Journal of Applied Physics, 26:215 (1987).*

Ashgriz, N., et al. Development of a Controlled Spray Generator. Rev. Sci. Instrum. 58(7):1291 (1987).*

Hikayama, H., et al. Ultrasonic Atomizer with Pump Function. Tech. Rpt. IEICE Japan US88–74:25 (1988).*

J. Acoustical Soc. Japan 44:2:116 (1988).*

J. Acoustical Soc. Japan 44:6:425 (1988).*
Siemens AG 1989, "Ink–Jet Printing: The Present State of the Art," by Wolfgang R. Wehl.*
TSI Incorporated product catalog. Vibrating Orifice Aerosol Generator (1989).*
Gaiser Tool Company catalog, pp. 26,29–30 (19_). (No date).*
Nogi, T., et al. Mixture Formation of Fuel Injection System in Gasoline Engine. Nippon Kikai Gakkai Zenkoku Taikai koenkai Koen Ronbunshu 69:660 (1991).*
D.C. Cipolla et al., "Assesment of Aerosol Delivery Systems for Recombinant Human Deoxyribonuclease," STP Pharma Sciences 4 (1) 50–62, 1994.
D.C. Cipolla et al., "Characterization of Aerosols of Human Recombinant Deoxyribonuclease I (rhDNase) Generated by Jet Nebulizers," Pharmaceutical Research II 94) 491–498, 1994.
I. Gonda, "Therapeutic Aerosols," Pharmaceutics, The Sci. of Dosage Form Design, M.E. Aulton, 341–358, 1988.
Anthony J. Hickey, "Pharmaceutical Inhalation Aerosol Technology," Drugs and the Pharmaceutical Sciences, (54) 172–173. No date.
A. Furuskär et al., "EDGE: Enhanced Data Rates for GSM and TDMA/136 Evolution," IEEE *Personal Communications Magazine*, pp. 56–66, Jun. 1999.
C.E. Gilchriest, "Signal–to–Noise Monitoring," *JPL Space Programs Summary*, vol. IV, No. 32–37, pp. 169–184, Jun. 1966.
J.W. Layland, "On S/N Estimation," *JPL Space Programs Summary*, vol. III, No. 37–48, pp. 209–212, 1967.

D.R. Pauluzzi and N.C. Beaulieu, "A Comparison of SNR Estimation Techniques in the AWGN Channel," *Proceedings of IEEE Pacific Rim Conference on Communications, Computers and Signal Processing*, pp. 36–39, 1995.
A.L. Rukhin, "Estimating the Noncentrality Parameter of A t–Distribution," *Systems Science and Mathematical Sciences*, vol. 5, No. 1, pp. 1–8, 1992.
K. Higuchi et al., "Experimental Evaluation of Combined Effect of Coherent Rake Combining and SIR–Based Fast Transmit Power Control for Reverse Link of DS–CDMA Mobile Radio," *IEEE Journal on Selected Areas in Comm.*, vol. 18, No. 8, pp. 1526–1535. (No date).
M.L. Tiku, "Doubly Noncentral F–Distributions—Tables and Applications," *Selected Tables in Mathematical Statistics*, vol. 2, pp. 139–149. (No date).
F.E. Satterthwaite, "An Approximate Distribution of Estimates of Variance Components," *Biometrika Bulletin*, vol. 2, pp. 110–114, 1946.
M.D. Austin and G.L. Stüber, "In–Service Signal Quality Estimation for TDMA Cellular Systems," *Proceedings of the Personal Indoor Mobile Radio Conference (PIMRC)*, pp. 836–840, Sep. 1995.
M. Andersin et al., "Subspace Based Estimation of the Signal to Interference Ratio for TDMA Cellular Systems," *Proceedings of the Vehicular Technology Conference (VTC)*, pp. 1155–1159, May 1996.

* cited by examiner

INSERT MOLDED AEROSOL GENERATOR AND METHODS

BACKGROUND OF THE INVENTION

This invention relates generally to the field of liquid droplet production, and in particular to the production of fine liquid droplets. More specifically, the invention relates to novel aerosol generators and manufacturing processes for producing such aerosol generators.

The ability to aerosolize or nebulize small liquid droplets is important to a variety of industries. Merely by way of example, many pharmaceuticals can now be delivered to the lungs in liquid form. Aerosolization is also a useful technique to dispense deodorizers, perfumes, insectizers or the like into the atmosphere.

One exemplary technology for producing fine liquid droplets is by supplying liquid to an aperture plate and vibrating the aperture plate to eject liquid droplets through the apertures. Such a technique is described generally in U.S. Pat. Nos. 5,164,740; 5,938,117; 5,586,550; 5,758,637 and 6,085,740, the complete disclosures of which are herein incorporated by reference.

This invention is related to manufacturing processes to produce aerosol generators utilizing such technology. The invention also relates to novel aerosol generators that may be manufactured in a low cost and/or high volume manner.

SUMMARY OF THE INVENTION

In one embodiment, a method is provided for producing an aerosol generator. The methods utilize a vibratable member having a plurality of apertures that are configured to produce liquid droplets when a liquid is applied to the vibratable member and the vibratable member is vibrated. According to the method, a support member is injected molded about the vibratable member, and a vibratable element is placed in vibrational communication with the vibratable member. In this way, an aerosol generator may be produced in a cost effective manner and in high volumes by injection molding the support element about the vibratable member.

In one aspect, the vibratable element and the vibratable member may be placed together in the mold before injection molding the support member. Alternatively, the vibratable element may be coupled to the support member after the injection molding process.

In some cases, a stiffening element may be placed between the vibratable element and the vibratable member to facilitate the transmission of vibrational energy from the vibratable element to the vibratable member. The stiffening element may be placed between the vibratable element and the vibratable member in a variety of ways. For example, the stiffening element may be placed into the mold along with the vibratable member. After injection molding the support member, the vibratable element may be coupled to the stiffening element. Alternatively, the vibratable element may be coupled to the stiffening element and then placed into the mold with the vibratable member where the support member is injection molded.

A variety of materials may be used to form the support member. Examples of materials that may be injection molded to form the support member include polystyrene, polysulfone, glass filled plastics, other plastics, and the like. In one particular aspect, the mold is configured to produce a support member that is cup shaped in geometry, although other shapes are possible, such as an annular ring. The vibratable member is placed into the mold such that an outer periphery of the vibratable member is surrounded by the support member, with a center portion of the vibratable member that has the apertures being free to receive and eject liquid. For example, a rear surface of the vibratable member that is within the cup may be supplied with liquid that is then ejected in the form of fine liquid droplets from the front surface upon actuation of the vibratable element.

In one configuration, the vibratable element may comprise an annular piezoelectric element that is disposed about the center portion of the vibratable member. The stiffening element may also be annular in geometry and be concentric with the piezoelectric element.

The invention further provides an aerosol generator that is constructed of a vibratable member having a front surface, a rear surface, an outer periphery and a central portion having a plurality of apertures. Preferably, the apertures taper from the rear surface to the front surface to permit fine liquid droplets to be produced through the apertures upon vibration. A support member is injection molded about the outer periphery such that the central portion is available to receive a liquid to be aerosolized. A vibratable element is in vibrational communication with the vibratable member to vibrate the vibratable member upon vibration of the vibratable element.

In one aspect, the vibratable element is an annular piezoelectric element that is coupled to the support member. Optionally a stiffening element, such as a rigid washer, may be placed between the piezoelectric element and the vibratable member. In another aspect, the support member may be constructed of a stiff material that is capable of being injection molded. In one particular aspect, the support member is injection molded into the shape of a cup, with the front surface of the vibratable member facing away from the cup.

In another embodiment, such an aerosol generator is placed within a housing to form an aerosolizer or nebulizer. The housing may conveniently include a mouthpiece so that aerosolized liquid may be delivered to a user's airway. A power supply to supply power to the piezoelectric element, and a supply of liquid may also be disposed within the housing.

DESCRIPTION OF THE SPECIFIC EMBODIMENTS

Figure 1:
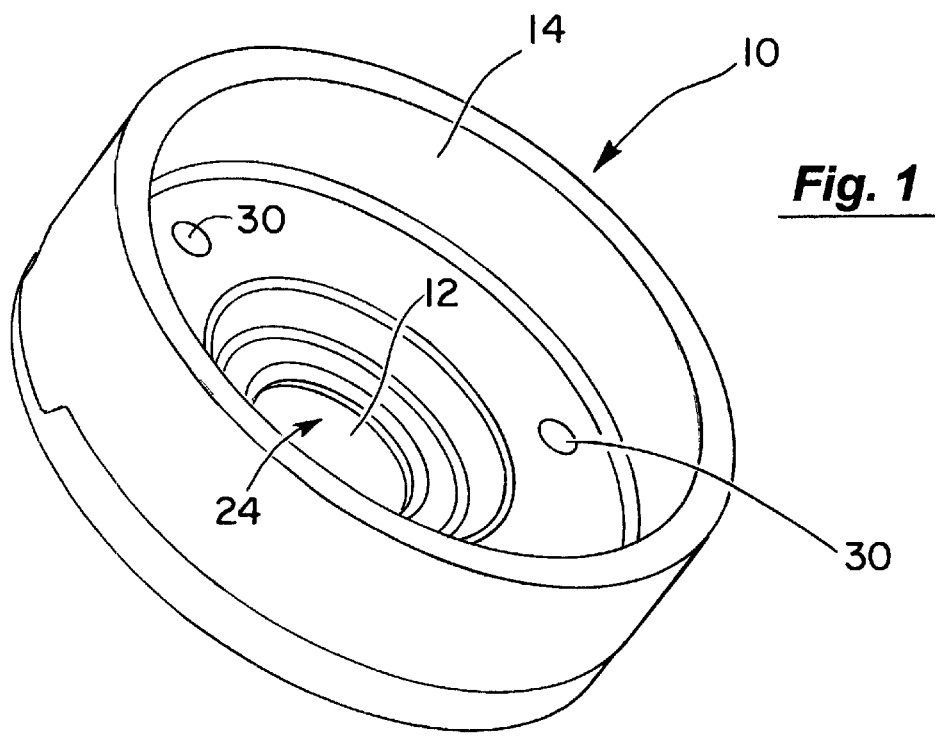
FIG. 1 is a rear perspective view of one embodiment of an aerosol generator according to the invention.

The invention provides ways to produce aerosol generators using an injection molding process. Such aerosol generators include a vibratable member having a plurality of apertures. Exemplary vibratable members that may be used with the invention include those described in U.S. Pat. Nos. 5,164,740; 5,938,117; 5,586,550; 5,758,637 and 6,085,740, incorporated herein by reference. However, it will be appreciated that the invention is not limited to only such vibratable members. The injection molding process is employed to create a support member about the vibratable member. The support member is used to hold the vibratable member and to permit vibrational energy from a vibratable element to be transmitted to the vibratable member. Techniques for vibrating the vibratable member with a piezoelectric element are described in, for example, U.S. Pat. Nos. 5,164,740; 5,938,117; 5,586,550; 5,758,637 and 6,085,740, incorporated herein by reference.

Because the support member needs to effectively transmit the vibrational energy, the support member is formed from a relatively stiff material, such as polyethylene, ryanite, polysulfone, glass filled plastic or the like. Optionally, one or more stiffening elements, such as a metal or ceramic washer, may be positioned adjacent to the piezoelectric element and the vibratable member to assist in transmitting the vibrational energy to the vibratable member. The stiffening member may be formed in a variety of shapes. For example, the support member may be cup or disc shaped in geometry. Other possible configurations include those described in copending U.S. patent application Ser. No. 09/848,104 filed on the same date as the present application, the complete disclosure of which is herein incorporated by reference.

To form the aerosol generator, the vibratable element (and optionally also the piezoelectric element and the stiffening element) are installed into a plastic injection mold. The mold is closed and the plastic is injected into the mold to form the plastic support member about he vibratable member. Optionally, the piezoelectric element or the stiffening element may be bonded to the support element after removal from the mold.

Such a process is particularly advantageous in that the aerosol generator may be manufactured in a low cost manner. Such a process also lends itself to high volume production. As such, the aerosol generators may cost effectively be placed into disposable aerosolizers, such as those used to deliver medicaments to the lungs. Further, by using high temperature plastics, an autoclaveable aerosol generator may be produced. In this way, the aerosol generator may be reused after being autoclaved. For example, such an aerosol generator may be incorporated into a ventilator in a health care facility. In this way, the aerosol generator may be reused after being autoclaved. Other uses for such aerosol generators include their incorporation into an inhaler that is reusable by the same individual thereby eliminating the need for autoclaving.

By using an injection molding process, it is possible to integrate the aerosol generator with other components in a single process. For example, the support member may be molded to a reservoir or container where liquids are to be stored. In this way, the aerosol generator and reservoir may be sold as a replacement item that is coupled to the reusable portion of an aerosolizer. For instance, the reservoir may contain a drug and may be coupled to an inhaler to provide the inhaler with a fresh supply of the drug. After depletion or expiration of the drug, the aerosol generator and reservoir may be removed, discarded and replaced.

Figure 2:
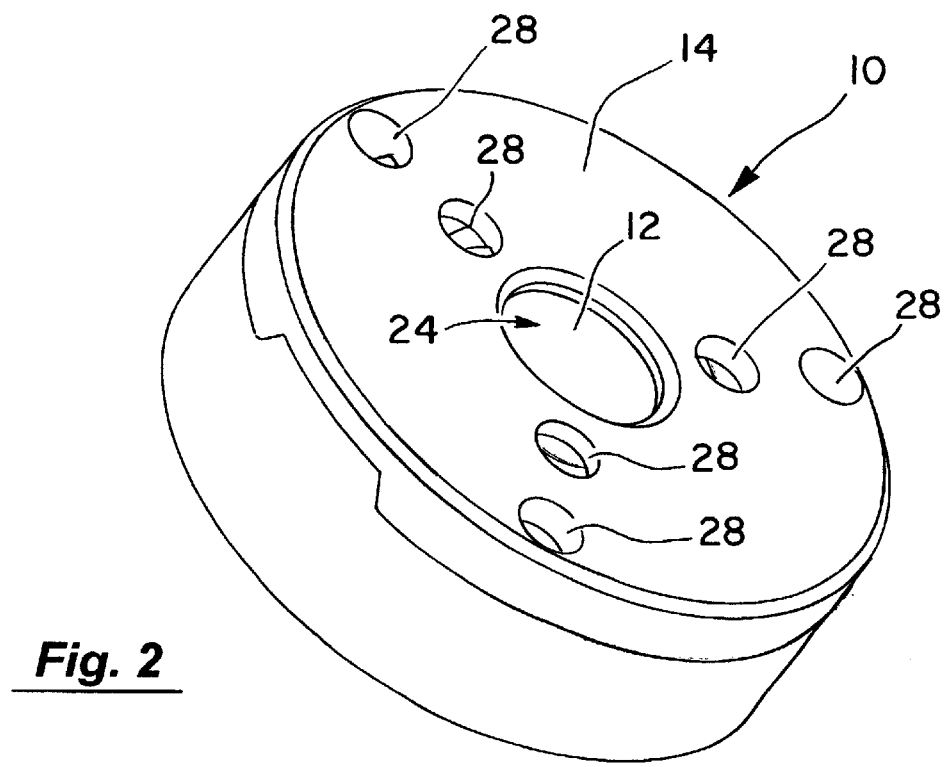
FIG. 2 is a front perspective view of the aerosol generator of FIG. 1.
Figure 4:
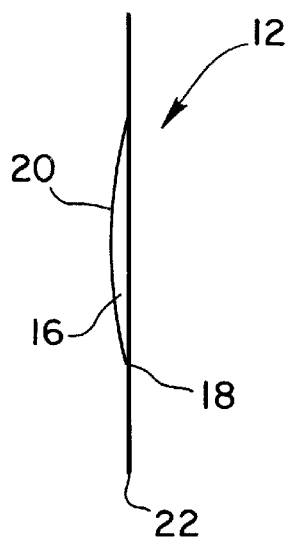
FIG. 4 is a side view of a vibratable member of the aerosol generator of FIG. 3.
Figure 5:
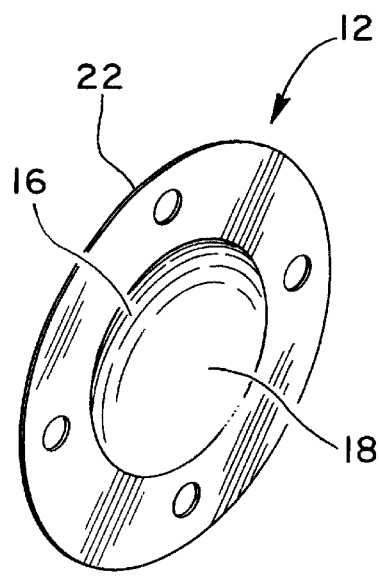
FIG. 5 is a rear perspective view of the vibratable member of FIG. 4.

Referring now to FIGS. 1 and 2, one embodiment of an aerosol generator 10 will be described. Aerosol generator 10 comprises a vibratable member 12 that is supported by a support member 14. Vibratable member 12 is shown separately in FIGS. 4 and 5 and comprises a dome-shaped plate having a rear 18, a front 20 and an outer periphery 22. Although not shown, plate 16 includes a plurality of apertures that taper from rear 18 to front 20. Such an aperture plate may be similar to those described in U.S. Pat. Nos. 5,586,550; 5,758,637 and 6,085,740, previously incorporated by reference. In use, a supply of liquid is provided to rear 18 and plate 16 is vibrated. Upon vibration, liquid droplets are ejected from front 20 as described generally in U.S. Pat. Nos. 5,586,550; 5,758,637 and 6,085,740, previously incorporated by reference.

Figure 3:
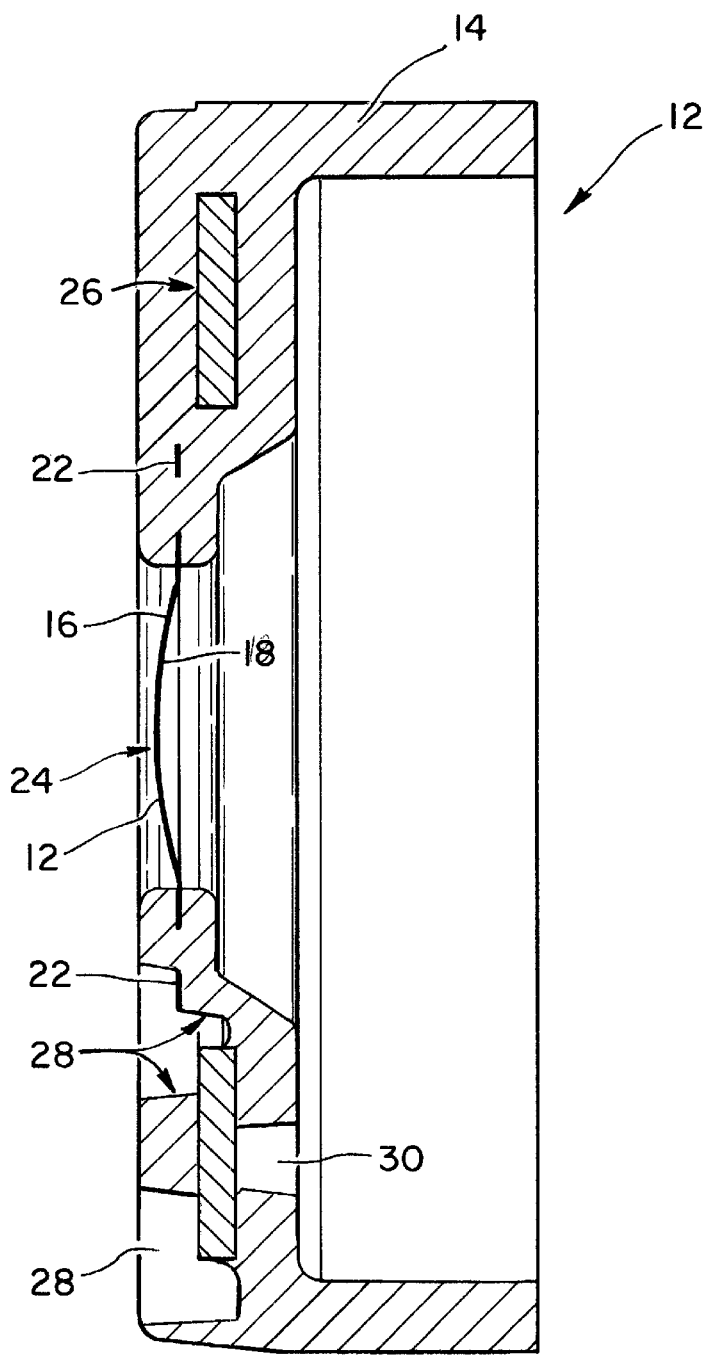
FIG. 3 is a cross sectional side view of the aerosol generator of FIG. 1.

Referring also now to FIG. 3, support member 14 is injection molded about periphery 22 of plate 16. A center portion of plate 16 having the tapered apertures is held across an opening 24 in support member 14 so that liquid droplets may be ejected front 20 when plate 16 is vibrated.

As shown, support member 14 is cupped shaped in geometry with rear 18 of plate 16 facing the interior of support member 14. However, it will be appreciated that support member 14 may be constructed of other shapes. Merely, by way of example, support member 14 may be constructed as an annular ring.

As best shown in FIG. 3, an annular vibratable element 26 is also injection molded into support member 14. Vibratable element 26 is preferably configured to vibrate at ultrasonic frequencies. One example of such a vibratable element is a piezo electric transducer. Vibratable element 26 is disposed within support member 14 so as to be concentrically aligned with opening 24. Although not shown, appropriate electrical leads will be provided to vibratable element 26 to supply electrical current to vibrate vibratable element 26. Upon vibration, the vibrational energy is transmitted through support member 14 and to vibratable member 12. In this way, a liquid may be aerosolized by placing liquid on rear 18 and energizing vibratable element 26.

To transmit the vibrational energy, support member 14 is preferably constructed of a relatively rigid material. Examples of materials that may be injection molded include plastics, such as polyethylene, ryanite, polysulfones, glass filled plastics and the like.

Figure 6:
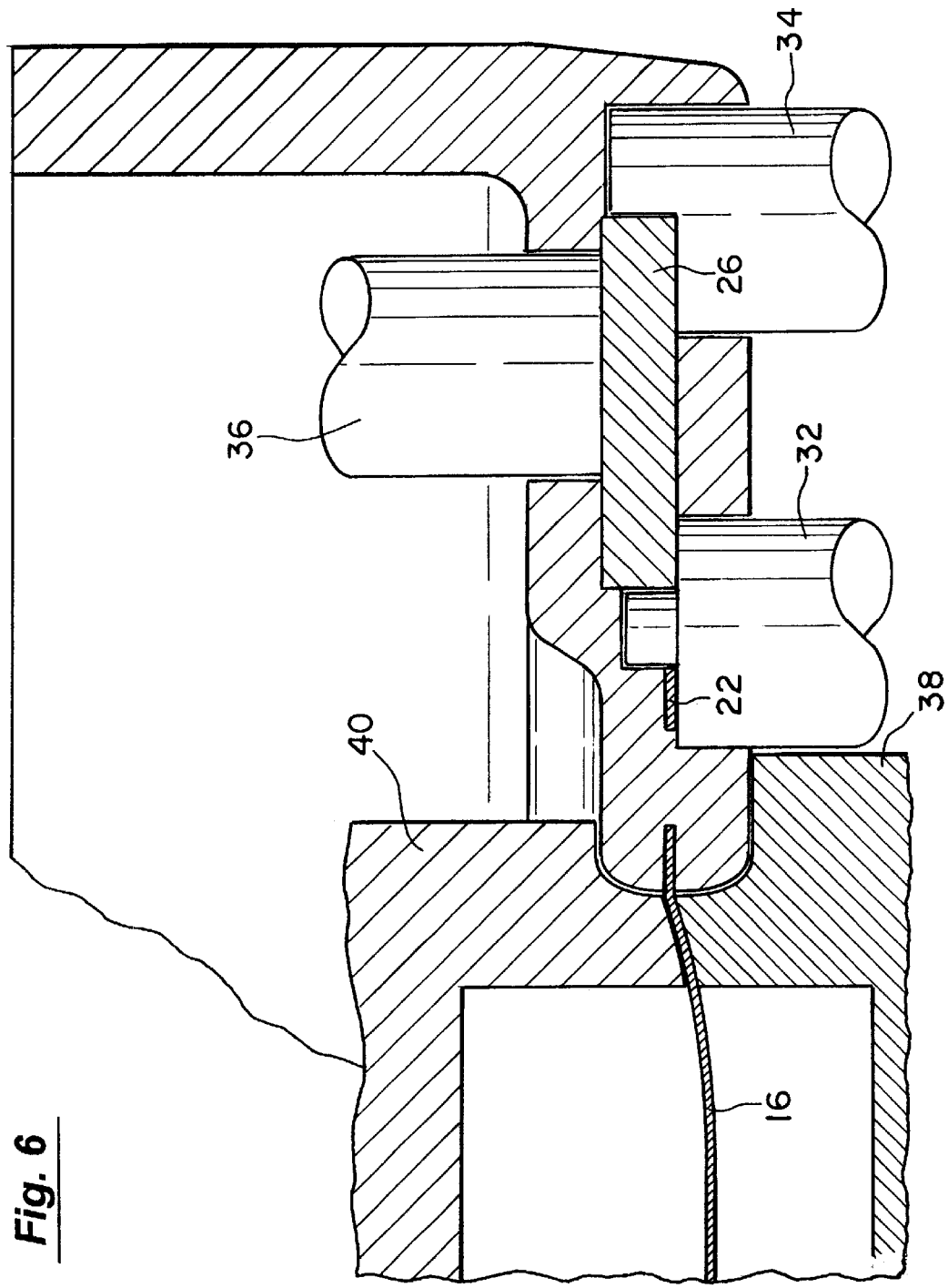
FIG. 6 illustrates a portion of the aerosol generator of FIG. 3 when being produced in an injection mold according to the invention.

Referring to FIGS. 1–3, support member 14 includes various holes 28 on the exterior surface and various holes 30 on the interior surface. Holes 28 and 30 are the result of the locator pins used in the injection molding process as illustrated in FIG. 6. To produce aerosol generator 10, vibratable element 26 is supported by rigid pins 32 and 34 as shown in FIG. 6. Although not shown, it will appreciated that three or more sets of such pins may be used. These pins are equally spaced about by vibratable element 26 to produce holes 28 at the end of the process. Conveniently, the process may utilize a vertical shuttle press to simplify insert molding. Positioned on top of vibratable element 26 are a set of spring-loaded pins 36 (only one being shown for convenience of illustration). Pins 32 are further configured to hold outer periphery 22 of plate 16. Plate 16 is also held in place by a steel support 38 and a spring-loaded center pin 40.

With plate 16 and vibratable element 26 held within the mold, heated plastic is injected into the mold. The plastic is then allowed to cool and harden, and then the mold is removed.

Figure 7:
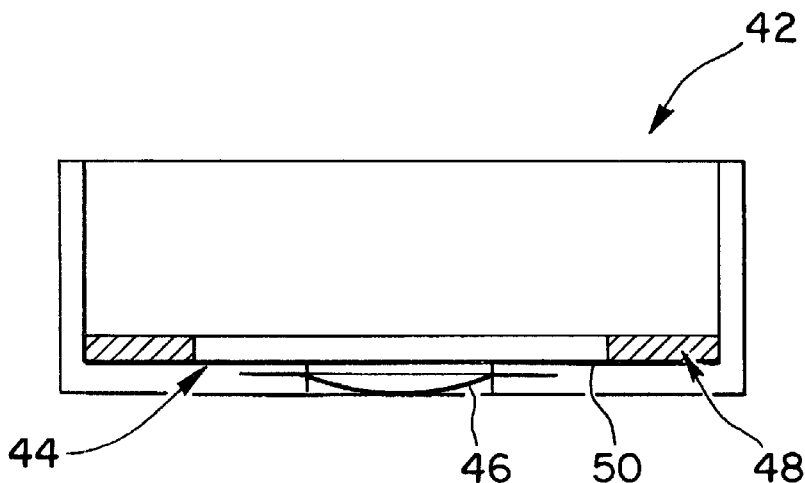
FIG. 7 is a cross sectional side view of another embodiment of an aerosol generator according to the invention.

In some cases, the vibratable element may be coupled to the support member after the aperture plate has been injection molded into the support member. An example of such a configuration is illustrated in FIG. 7. In the embodiment of FIG. 7, an aerosol generator 42 has a support member 44 that is injection molded about a vibratable member 46 in a manner similar to that described in connection within aerosol generator 10. After the injection molding process, an annular vibratable element 48 is bonded to support member 44 using a bonding agent 50. By bonding vibratable element 48 to support member 44 after the injection molding process, the chances of damaging vibratable element 48 within the mold is reduced. Further, the mold is simplified allowing for an easier injection molding process.

Figure 8:
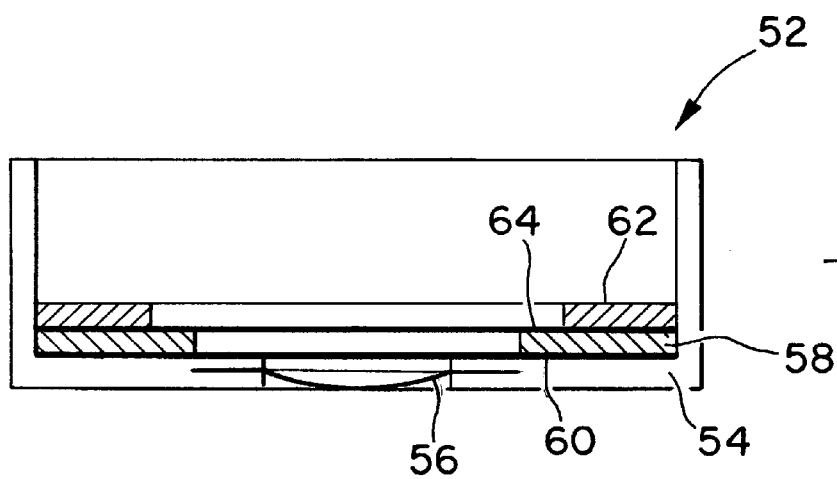
FIG. 8 is a cross sectional side view of a further embodiment of an aerosol generator according to the invention.
Figure 9:
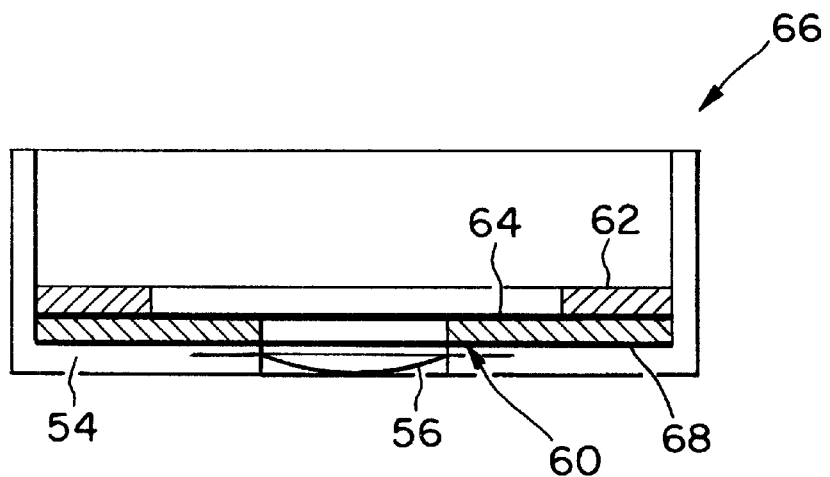
FIG. 9 is a cross sectional side view of still another embodiment of an aerosol generator according to the invention.

In some cases, it may be desirable to insert a stiffening element between the piezo electric transducer and the aperture plate. Such embodiments are illustrated in FIGS. 8 and 9. In FIG. 8, an aerosol generator 52 comprises a support member 54 that is injection-molded about a vibratable member 56 in a manner similar to that previously described in connection with FIG. 7. Following the injection molding process, a stiffening element 58, such as annular washer, is bonded to support member 54 using a bonding agent 60. A vibratable element 62 is bonded to stiffening element 58 by use of a bonding agent 64. Stiffening element 58 may be used to provide a stiffer structure to more efficiently transmit the vibrational energy from vibratable element 62 to vibratable member 56. Materials that may be used to construct stiffening element 56 include aluminum, stainless steel, other metals, ceramics, and the like.

FIG. 9 illustrates an aerosol generator 66 that is essentially identical to aerosol generator 52 except that a different sized stiffening element 68 is employed. For convenience of illustration, the other elements will use the same reference numerals used to describe aerosol generator 52 of FIG. 8. Stiffening element 68 has a smaller internal diameter that circumscribes a center portion of vibratable member 58 that includes the apertures. The reduced diameter stiffening element is useful in reducing the stiffener mass and in producing higher aerosolization rates.

Figure 10:
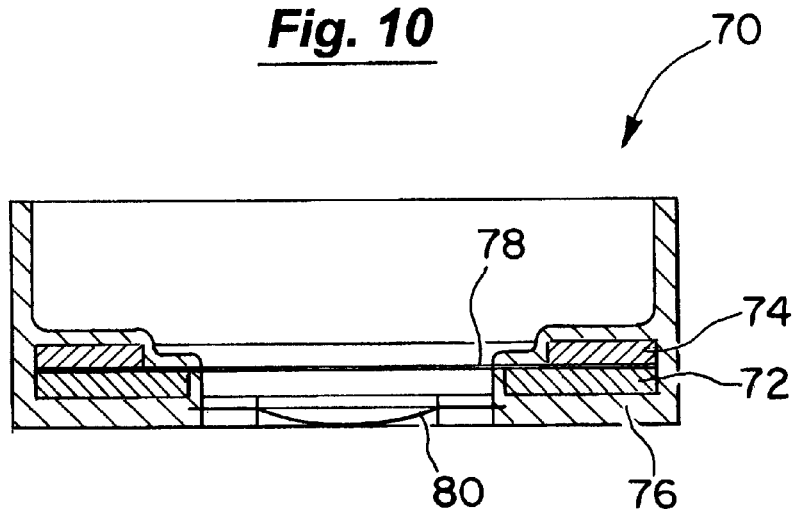
FIG. 10 is a cross sectional side view an yet another embodiment of an aerosol generator according to the invention.

FIG. 10 illustrates an aerosol generator 70 where a stiffening element 72 and a vibratable element 74 are injection-molded into a support member 76. To construct aerosol generator 70, stiffening element and vibratable element 74 may be bonded together with a bonding agent 78 and then placed into the mold along with a vibratable member 80. Plastic may then be injected into the mold to form support member 76.

Figure 11:
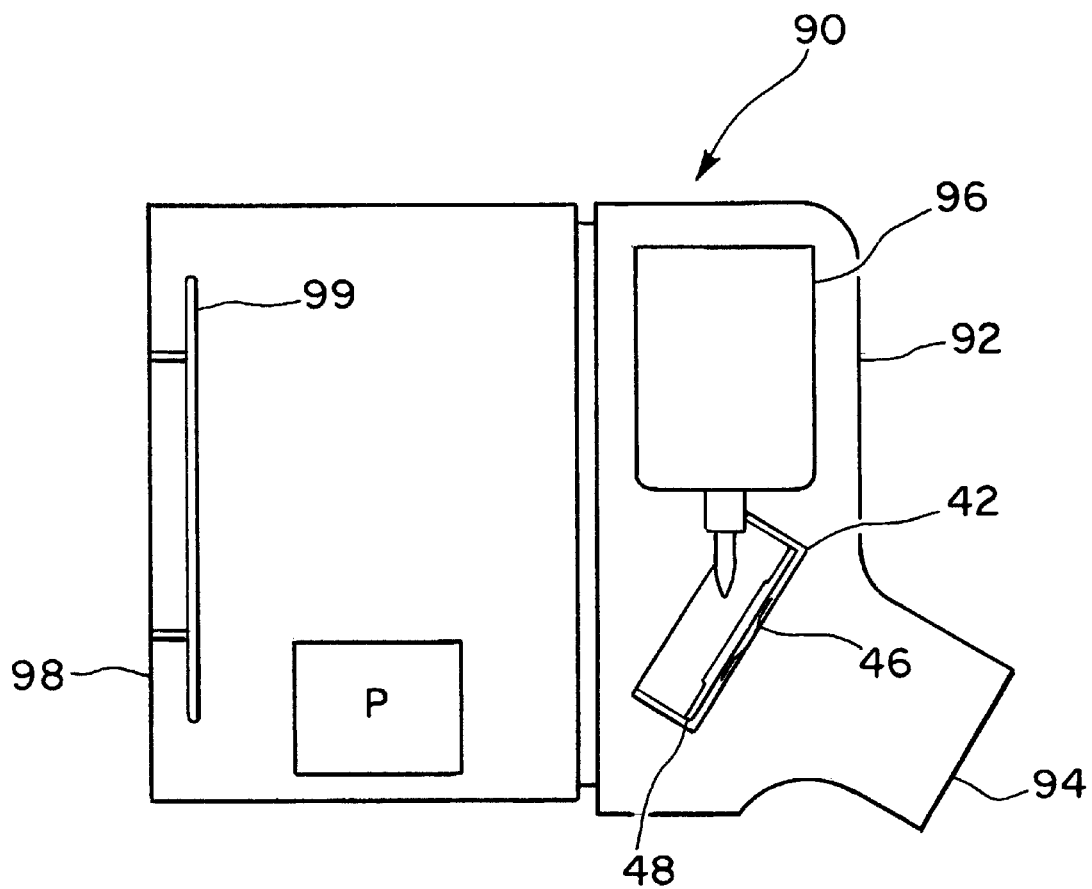
FIG. 11 illustrates the aerosol generator of FIG. 1 when placed into an aerosolization device.

FIG. 11 illustrates an aerosolization device 90 will be described. Device 90 comprises a housing 92 to hold the various components of aerosolization device 90. Housing 92 further includes a mouthpiece 94 and one or more vents (not shown) to permit air to enter into housing 92 when a user inhales from mouthpiece 94. Disposed within housing 92 is insert molded aerosol generator 42 of FIG. 7. However, it will be appreciated that any of the aerosol generators described herein may be placed into housing 92.

Aerosolization device 90 further includes a canister 96 having a supply of liquid that is to be aerosolized by aerosol generator 42. Canister 96 may include a metering valve to place a metered amount of liquid onto aperture plate 46. Although not shown, a button or the like may be employed to dispense the volume of liquid when requested by the user.

Housing 92 includes an electronics region 98 for holding the various electrical components of aerosolization device 90. For example, region 98 may include a printed circuit board 99 which serves as a controller to control operation of the aerosol generator 42. More specifically, circuit board 99 may send (via circuitry not shown) an electrical signal to the piezoelectric element 48 to cause aperture plate 46 to be vibrated. A power supply P, such as one or more batteries, is electrically coupled to circuit board 99 to provide aerosolization device 90 with power.

Figure 12:
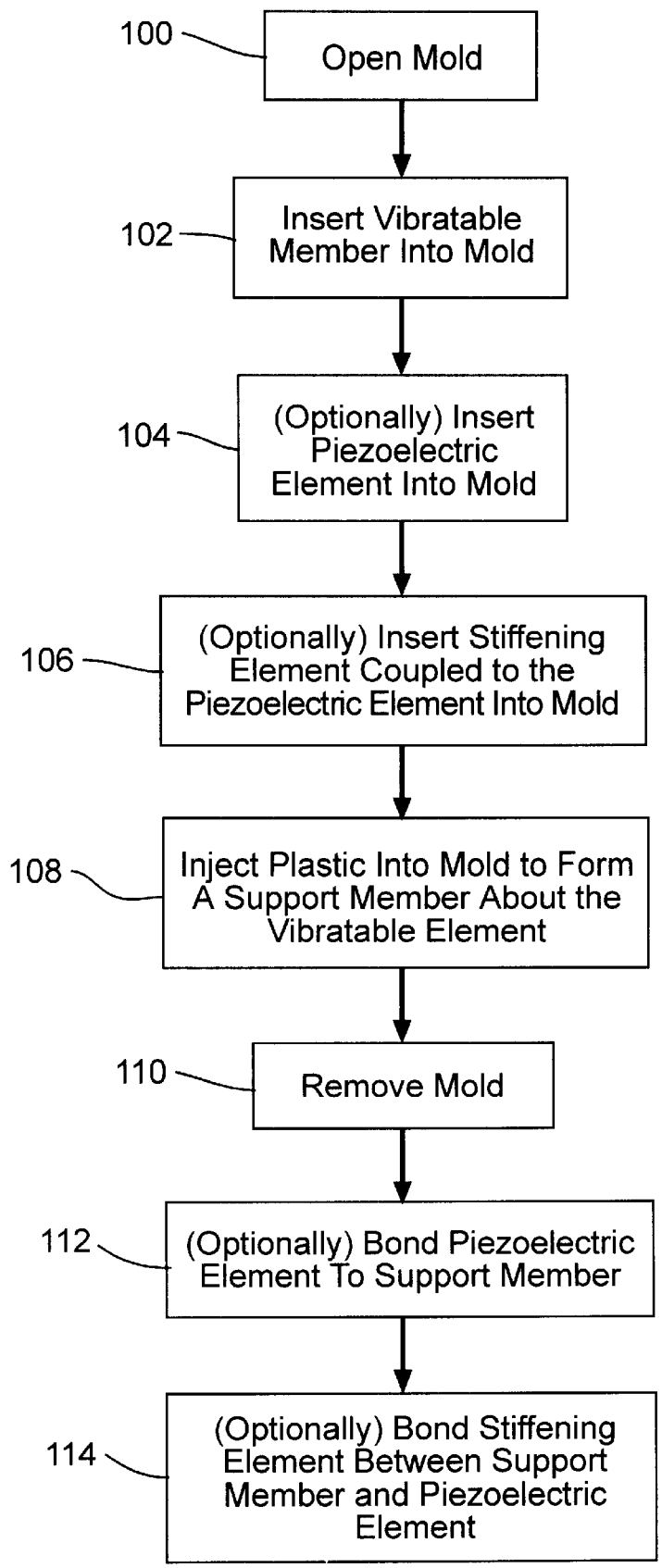
FIG. 12 is a flow chart illustrating one method for producing an aerosol generator according to the invention.

Referring now to FIG. 12, one method for producing an aerosol generator using an injection mold and process will be described. Initially, the mold is opened as illustrated in step 100 and the vibratable member is inserted into the mold as illustrated in step 102. Optionally, a piezo electric element may also be inserted into the mold as illustrated in step 104 if it is desired to have the piezo electric element incorporated into the support element. As shown in step 106, a stiffening element may optionally be coupled to the piezo electric element, with the combined structure being placed into the mold.

In step 108, plastic is injected into the mold to form a support member about the vibratable element. If the stiffening element and/or the piezo electric element are also placed into the mold, the support member will also be formed around these structures as well. After the plastic has cooled, the mold is removed as shown in step 110.

In the optional step of 112, a piezo electric element may be bonded to the support member, assuming that it was not previously injection-molded into a support member. In a similar manner (as illustrated in step 114), a stiffening element may be bonded between the support member and the piezo electric element if these components were not previously incorporated into the support member.

The invention has now been described in detail for purposes of clarity of understanding. However, it will be appreciated certain changes and modifications may be practiced within the scope of dependent claims.

What is claimed is:

1. A method for producing an aerosol generator, the method comprising:

providing a vibratable member having a plurality of apertures that are configured to produce liquid droplets upon vibration of the vibratable member, the vibratable member having a front surface, a back surface, and an outer periphery, wherein vibrations of the vibrating member causes the plurality of apertures to be displaced and liquid to move through the apertures from the back side to the front side thereby nebulizing the fluid;

injection molding a support member about the vibratable member, the vibratable member being injection molded to surround the outer periphery of the vibratable member, wherein a center of the vibratable member having the apertures is available for receiving a liquid to be aerosolized; and placing a vibratable element in vibrational communication with the vibratable member.

2. A method as in claim 1, further comprising placing the vibratable element adjacent to the vibratable member prior to the injection molding step.

3. A method as in claim 1, further comprising coupling the vibratable element to the support member after the injection molding step.

4. A method as in claim 1, further comprising placing a stiffening element between the vibratable member and the vibratable element.

5. A method as in claim 1, further comprising attaching the vibratable element to the stiffening element after the injection molding step.

6. A method as in claim 4, further comprising coupling the stiffening element to the vibratable element and placing the stiffening element adjacent to the vibratable member prior to the injection molding step.

7. A method as in claim 1, wherein the injection molding step further comprises placing at least the vibratable member into a mold and injecting heated material into the mold to form the support member.

8. A method as in claim 7, wherein the heated material comprises a plastic, and wherein the mold has a cup shaped cavity to form the support member in the shape of a cup.

9. A method as in claim 1, wherein the vibratable element comprises an annular piezoelectric element that is disposed about the center of the vibratable member.

10. A method as in claim 4, wherein the stiffening element comprises an annular washer that is concentrically aligned with the vibratable element.

11. A method of nebulizing a fluid, comprising the steps of:

providing a vibrating element and a vibrating member, the vibrating member being vibrated by the vibrating element, the vibrating member having a plurality of apertures extending from a front side to a back side of the vibrating member, the vibrating member also having an outer perhiphery surrounding the plurality of apertures;

injection molding a supporting element around the outer periphery of the vibrating member to embed the outer periphery in the supporting element, the supporting element being injection molded to form an opening in the supporting element with the vibrating member extending across the opening, the supporting element also being injection molded around at least part of the vibrating element;

delivering a fluid to the back side of the vibrating member;

vibrating the vibrating element so that the vibrating member vibrates to displace the plurality of apertures, wherein the fluid at the back side of the vibrating member passes through the plurality of apertures as the plurality of apertures are displaced thereby nebulizing the fluid.

12. A method as in claim 11, further comprising placing the vibratable element adjacent to the vibratable member prior to the injection molding step.

13. A method as in claim 11, further comprising placing a stiffening element between the vibratable member and the vibratable element.

14. A method as in claim 13, further comprising coupling the stiffening element to the vibratable element and placing the stiffening element adjacent to the vibratable member prior to the injection molding step.

15. A method as in claim 11, wherein the molding step is carried out with a mold having a cup shaped cavity to form the support member in the shape of a cup.

16. A method as in claim 11, wherein the vibratable element comprises an annular piezoelectric element that is disposed about the center of the vibratable member.

17. A method as in claim 14, wherein the stiffening element comprises an annular washer that is concentrically aligned with the vibratable element.

* * * * *